United States Patent [19]

Andersen et al.

[11] Patent Number: 5,106,969
[45] Date of Patent: Apr. 21, 1992

[54] BIOLOGICALLY ACTIVE THIAZINE

[75] Inventors: Raymond J. Andersen, Vancouver; Theresa M. Allen, Edmonton; E. Dilip de Silva, Vancouver; Julie S. Racok, Edmonton, all of Canada; Jon Clardy; Linda S. Brinen, both of Ithaca, N.Y.

[73] Assignees: Cornell Research Foundation, Inc., Ithaca, N.Y.; The University of Alberta, Edmonton; The University of British Columbia, Vancouver, both of Canada

[21] Appl. No.: 683,457

[22] Filed: Apr. 11, 1991

[51] Int. Cl.⁵ .......................... C07D 513/04
[52] U.S. Cl. ............................... 544/48
[58] Field of Search ........................ 544/48

[56] References Cited

U.S. PATENT DOCUMENTS 4,898,878  2/1990  Shapiro et al. ................ 514/386

OTHER PUBLICATIONS

DeSilva et al., Chemical Abstracts, vol. 115, entry 89448r (1991).
Cordes, A. W. et al., Acta Cryst. C42, 508-509 (1986).
Gieren, A. et al., J. Am. Chem. Soc, 101, 7277-7281 (1979).
Holler, T. P. et al., J. Org. Chem. 54, 4570-4575 (1989).
Palumbo, A, Comp. Biochem. Physiol, 78B, 81-83 (1984).

Primary Examiner—John M. Ford

[57] ABSTRACT

5-Methylimidazo[4,5-e]-1,2-thiazin-4(5-H)-one, having the structure

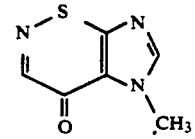

a cytotoxic metabolite of the marine sponge *Neamphius huxleyi*, has been isolated from the sponge by extraction and chromatography.

1 Claim, No Drawings

BIOLOGICALLY ACTIVE THIAZINE

This invention was made in part with Government support under National Institutes of Health grant number CA24487; the Government has certain rights in the invention. Other financial support was provided by the National Cancer Institute of Canada, the Natural Sciences and Engineering Research Council and The New York Sea Grant.

TECHNICAL FIELD

This invention is directed to the discovery of 5-methylimidazo[4,5-e]-1,2-thiazin-4(5H)-one.

BACKGROUND OF THE INVENTION

The multitude of plant and animal species have been recognized as a potential source of biologically active compounds. A number of compounds have been isolated from marine invertebrates, and some of these have been found to be cytotoxic and antineoplastic. In view of this, marine invertebrates are being gathered and compounds are being recovered from them and screened for biological activity.

It is an object of this invention to discover and isolate a previously unknown biologically active compound from a marine invertebrate.

SUMMARY OF THE INVENTION

The invention herein provides for the first time substantially pure compound having the structural formula

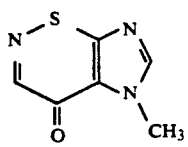

and having the systematic name 5-methylimidazo[4,5-e]-1,2-thiazin-4(5H)-one. The structure of the compound has been confirmed by single crystal X-ray diffraction analysis. The compound has antiviral, antitumor and immune system stimulatory functionality.

The term "substantially pure" is used herein to mean greater than 99% pure on a solvent free basis.

DETAILED DESCRIPTION

The compound herein is a metabolite of a ruby-colored, encrusting, marine, cake sponge and is recoverable therefrom as described below. The sponge specimens that constituted the source of the compound were collected by hand from growth on living coral on near-shore reefs off Sek Point, Madang, Papua, New Guinea. The collected sponge specimens were identified as being of the species *Neamphius huxleyi* (Sollas, 1888) by Dr. R. van Soest, of the Institute for Taxonomic Zoology, Zoological Museum, University of Amsterdam, and a voucher specimen is deposited at said Zoological Museum.

The compound herein is the first compound known to have the imidazo[4,5-e]-1,2-thiazine ring system and has been termed neamphine by inventors herein because of its discovery in *Neamphius huxleyi*.

Substantially pure compound is readily recovered from sponge source by extracting with methanol/dichloromethane, concentrating the extract to obtain a gummy residue, partitioning between water/methanol and chloroform, concentrating the more polar phase, extracting the concentrate with ethyl acetate, fractionating the ethyl acetate soluble materials utilizing isocratic silica gel chromatography first with dichloromethane/methanol to obtain a partially purified product and then with hexane/ethyl acetate, and then recrystallizing using hexane/chloroform.

For antiviral use, the compound is administered systemically to an infected mammal in a substantially non-toxic antiviral effective dose.

For antitumor use, the compound is administered systemically to a mammal bearing a tumor in a substantially non-toxic antitumor effective dose.

For immune system stimulation, the compound is administered systemically to a mammal in need of such stimulation in a substantially non-toxic immune stimulating effective dose.

The compound herein is intended for use parenterally or orally. It is readily distributed as a dry pharmaceutical composition containing diluents, buffers, stabilizers, solubilizers, and ingredients contributing to pharmaceutical elegance. For injection, the compound herein is readily administered in a liposome system.

The invention is illustrated by the following example:

EXAMPLE

Two pieces of the sponge *Neamphius huxleyi*, collected as described above, were utilized. Both pieces were basically round. The larger piece was 3 to 4 inches in diameter and 1½ to 2 inches thick, and the smaller piece was 2 inches in diameter and 1 inch thick.

The freshly collected sponge (320 g dry weight) was frozen by placing it in a normal freezer located at a marine station near the collection site. It was thereafter transported frozen to the University of British Columbia on dry ice. The frozen sponge was thawed by immersion in one liter of 1:1 methanol/dichloromethane and the thawed samples were extracted in said liquid. The resulting extract was concentrated in a rotary evaporator to provide a gummy residue. The residue was immersed in and partitioned between phases of an admixture of 500 ml of 6:4 methanol/water and 500 ml of chloroform. On separation of the phases, the more polar phase which constituted an aqueous suspension was recovered and was concentrated utilizing a rotary evaporator to give 25 ml that was diluted with water to give a 500 ml aqueous suspension. This 500 ml aqueous suspension was extracted 3 times using a fresh 200 ml of ethyl acetate for each extraction. The resulting extracts were combined to give 600 ml of ethyl acetate extract and this was concentrated in a rotary evaporator to give a residue that was subjected to chromatography. Chromatographic separation consisted of isocratic silica gel chromatography eluting in the first instance with 96:4 dichloromethane/methanol and in the second instance with 1:2 hexane/ethyl acetate. Recrystallization from 2:1 hexane/chloroform gave 0.6 mg colorless needles of 5-methylimidazo[4,5-e]-1,2-thiazin-4(5H)-one, 99.9+% pure (NMR).

The compound gave an intense parent ion in the Electron Impact High Resolution Mass Spectrum at m/z 167.0153 Da appropriate for a molecular formula of $C_6H_5N_3OS$ ($\Delta M$ -0.1 mmu).

The $^1H$ nmr spectrum (400 MHz, $CDCl_3$) contained three singlets at $\delta$ 4.18 (3H), 7.84 (1H) and 8.63 (1H) that could be assigned to a methyl group attached to a heteroatom and two heterocyclic aromatic protons, respectively.

A strong absorption band at 1625 cm$^{-1}$ in the ir spectrum was tentatively assigned to a carbonyl stretching vibration.

Single crystal X-ray diffraction analysis was carried out as follows: A flat needle (0.1×0.2×0.7 mm) was selected and preliminary X-ray examination revealed monoclinic symmetry with lattice constants of a=7.837(5), b=3.880(3), c=11.518 (9) Å, and $\beta$=97.09(6)°. Systematic extinctions and density considerations led to space group P2$_1$ with one molecule of composition C$_6$H$_5$N$_3$OS in the asymmetric unit. All diffraction maxima with 2Θ≦45° were collected with a computer controlled four-circle diffractometer using Θ:2Θ scans and graphite monochromated Mo Kα radiation. A total of 527 unique reflections were measured and after correction for Lorentz, polarization, and background effects, 460(87%) were judged observed ($|F_o| \geq 5\sigma(|F_o|)$). A phasing model was found easily using direct methods. Full-matrix least-squares refinements with anisotropic riding hydrogen atoms converged to a final crystallographic residual of 3.61% which is indicative of the correctness of the structure set forth above.

In vitro testing was carried out using L1210/c2 murine leukemia cell lines obtained from the McEachern Institute at the University of Alberta according to National Cancer Institute Protocol as set forth in NIH Publication No. 84-2635 "In Vivo Cancer Model". In the testing the culture medium used was Fischer's Medium supplemented with 10% heat inactivated horse serum with 1% antibiotics. 10$^5$ cells of L1210/c2 were used per ml of culture medium. Selected concentrations of the subject compound dissolved in ethanol were added to culture medium with L1210/c2 cells therein and growth of L1210/c2 cells was compared to where subject compound was not added. The effective dose for inhibiting growth of the L1210/c2 cells by 50% compared to the control (ED$_{50}$) was found to be less than 10 μg/ml. According to said Protocol, an ED$_{50}$ of 10 μg/ml or less is considered to suggest potential for in vivo antineoplastic activity and constitutes an indication for conducting in vivo testing.

Variations in the invention will be obvious to those skilled in the art. Therefore the invention is defined by the claim.

What is claimed is:

1. Substantially pure compound having the structure

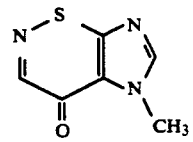

* * * * *